(12) United States Patent
Grant et al.

(10) Patent No.: US 7,358,096 B1
(45) Date of Patent: Apr. 15, 2008

(54) IMMOBILISATION OF PROTEINS

(75) Inventors: Steven Daryl Grant, Shambrook Bedford (GB); Steven Howell, Shambrook Bedford (GB); Stephen Wilson, Shambrook Bedford (GB)

(73) Assignee: Conopco, Inc., Edgewater, NJ (US)

( * ) Notice: Subject to any disclaimer, the term of this patent is extended or adjusted under 35 U.S.C. 154(b) by 602 days.

(21) Appl. No.: 10/129,012

(22) PCT Filed: Nov. 22, 2000

(86) PCT No.: PCT/EP00/11625

§ 371 (c)(1),
(2), (4) Date: Oct. 29, 2002

(87) PCT Pub. No.: WO01/40310

PCT Pub. Date: Jun. 7, 2001

(30) Foreign Application Priority Data

Nov. 29, 1999 (EP) .................................. 99309515

(51) Int. Cl.
*G01N 33/543* (2006.01)

(52) U.S. Cl. .................. 436/518; 436/501; 436/824; 435/7.1; 435/7.92; 435/824; 530/300

(58) Field of Classification Search ................ 435/7.1, 435/7.92–7.94, 69.7, 287.7; 436/501, 518, 436/524–527, 86, 823, 824; 530/300
See application file for complete search history.

(56) References Cited

U.S. PATENT DOCUMENTS

| 4,894,443 | A |   | 1/1990  | Greenfield et al. | ......... | 530/388 |
| 5,089,605 | A | * | 2/1992  | Profy et al. | ............... | 530/388.1 |
| 5,518,889 | A |   | 5/1996  | Ladner et al. | ............. | 435/7.93 |
| 5,948,894 | A | * | 9/1999  | Berry et al. | ............. | 530/391.1 |
| 6,274,324 | B1 | * | 8/2001  | Davis et al. | ................. | 435/7.1 |
| 6,329,209 | B1 | * | 12/2001 | Wagner et al. | ............. | 436/518 |

FOREIGN PATENT DOCUMENTS

| EP | 0497585 |   | 1/1992 |
| GB | WO 94/04678 | * | 3/1994 |
| WO | WO 91/08482 |   | 11/1990 |

OTHER PUBLICATIONS

Creighton, Proteins: Structures and Molecular Properties, 1984, pp. 314-316.*

Strauss and Goetz (1996), "In vivo immobilization of enzymatically active polypeptides on the cell surface of *Staphylococcus carnosus*," *Molecular Microbiology* 21:491-500; Database Biosis 'Online! Biosciences Information Service, Philadelphia, PA 1996.

* cited by examiner

*Primary Examiner*—Long V. Le
*Assistant Examiner*—Gary W. Counts
(74) *Attorney, Agent, or Firm*—Morgan, Lewis & Bockius LLP

(57) ABSTRACT

The immobilization of proteins at solid surfaces facilitated by incorporation of a polypeptide segment which is capable of adopting a folded structure is described. Materials comprising proteins so immobilized and uses thereof are also described.

13 Claims, 3 Drawing Sheets

Fig. 1.

```
SW26 5' TC GAG CAC CAT CAC CAT CAC CAT CGT TCT GGT AAG GGT AAG
SW27 3'     C GTG GTA GTG GTA GTG GTA GCA AGA CCA TTC CCA TTC
Protein        E   H   H   H   H   H   H   R   S   G   K   G   K SW26        AAG GGA AAG GGT AAG GGT AAG TAA TAA C           3'
SW27        TTC CCT TTC CCA TTC CCA TTC ATT ATT GTT AA      5'
Protein      K   G   K   G   K   G   K   .   .   L SW28 5' TC GAG CAC CAT CAC CAT CAC CAT CGT TCT GGT AAG GGT AAG
SW29 3'     C GTG GTA GTG GTA GTG GTA GCA AGA CCA TTC CCA TTC
Protein        E   H   H   H   H   H   H   R   S   G   K   G   K SW28        AAG CCA AAG GGT AAG GGT AAG TAA TAA C           3'
SW29        TTC GGT TTC CCA TTC CCA TTC ATT ATT GTT AA      5'
Protein      K   P   K   G   K   G   K   .   .   L SW30 5' TC GAG CAC CAT CAC CAT CAC CAT CGT TCT GAG AAG GAG AAG
SW31 3'     C GTG GTA GTG GTA GTG GTA GCA AGA CTC TTC CTC TTC
Protein        E   H   H   H   H   H   H   R   S   E   K   E   K SW30        AAG CCA AAG GAG AAG GAG AAG TAA TAA C           3'
SW31        TTC GGT TTC CTC TTC CTC TTC ATT ATT GTT AA      5'
Protein      K   P   K   E   K   E   K   .   .   L
```

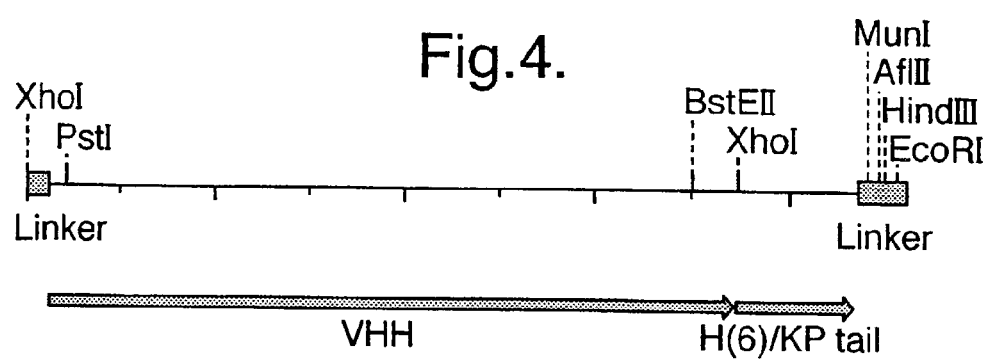
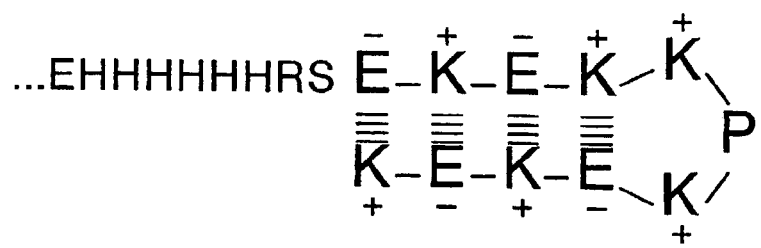
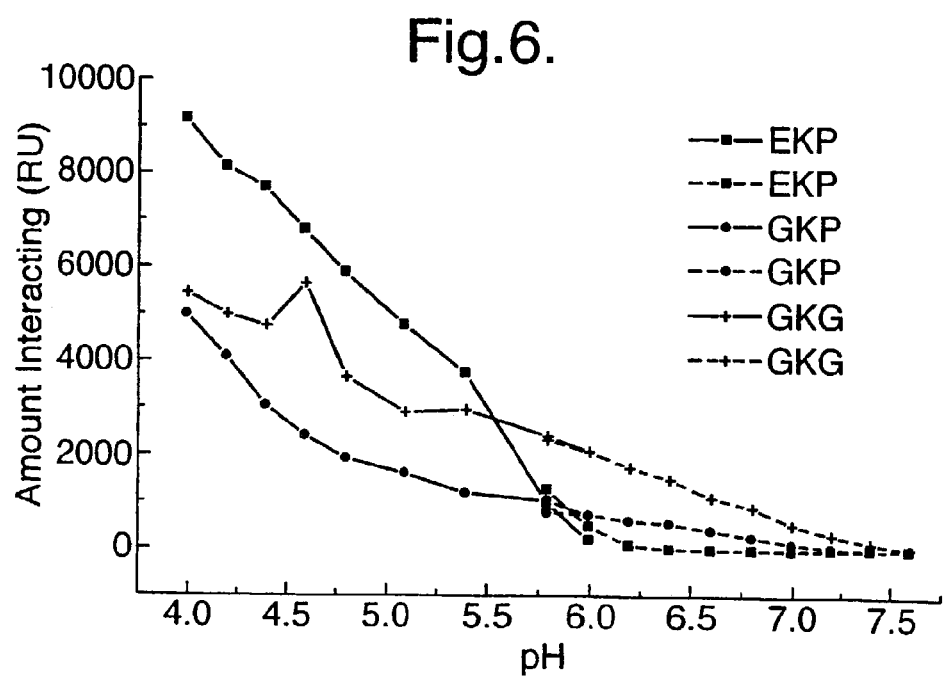

IMMOBILISATION OF PROTEINS

FIELD OF THE INVENTION

The present invention relates generally to the immobilisation of proteins at solid surfaces. More particularly, the invention relates to the preparation and use of materials, especially immunoactive materials, comprising a protein immobilised on a solid surface by means of a polypeptide segment comprising one or more sites for covalent linkage, which segment is capable of adopting a folded structure.

BACKGROUND OF THE INVENTION

Processes directed towards immobilising proteins on to a solid surface are of considerable commercial interest. Functionalisation of surfaces with immunological materials, such as antibodies or antibody fragments, for example, forms the basis of immunoadsorption techniques such as immuno affinity purification processes which are increasingly being applied to the recovery or purification of a range of commercially important materials.

Commonly, attachment of proteins to solid surfaces, such as chromatography media, has been brought about by exposing the surface to a solution of the protein such that the protein is adsorbed onto the solid surface via non-specific binding mechanisms. Methods for immobilising proteins on chromatography media are well established in the literature (see for example, In Protein Immobilisation, R. F. Taylor ed., Marcel Dekker, Inc., New York, 1991). Where the solid surface is provided by a hydrophobic material such as polystyrene, for example, then attachment is generally brought about by adsorption of hydrophobic regions of the protein onto the hydrophobic surface.

Adsorption onto the solid surface is usually accompanied by significant conformational disruption with partial unfolding and denaturation of the protein concerned. The concomitant loss of protein activity detracts from the overall usefulness of the process. Commonly, for example, adsorption of antibodies onto a hydrophobic surface is accompanied by the loss of in the order of greater than 95% of specific binding activity. Where smaller antibody fragments are involved, the amount of specific binding affinity retained upon adsorption onto a solid surface can be even lower as described in Molina-Bolivar et al, J. Biomaterials Science-Polymer Edition, 9, 1103-1113, 1998).

Alternatives to or improvements upon the method of adsorption of proteins in the preparation of immobilised protein surfaces have been considered.

One alternative approach is to use chemical cross-linking of residues in the protein for covalent attachment to an activated solid surface using conventional coupling chemistries for example as described in Bioconjugate Techniques, G. T. Hermanson, ed. Academic Press, Inc., San Diego, Calif., USA. Amino acid residues incorporating sulphydryl groups, such as cysteine, may be covalently attached using a bispecific reagent such as succinimidyl-maleimidophenyl-butyrate (SMPB), for example. Alternatively, lysine groups located at the protein surface may be coupled to activated carboxyl groups at the solid surface by conventional carbodiimide coupling using 1, ethyl-3-[3-dimethyl aminopropyl] carbodiimide (EDC) and N-hydroxysuccinimide (NHS). A disadvantage of this approach is that cross-linking residues in the protein can interfere with the functionality of the protein.

By providing the protein with a peptide tail extension containing cross-linkable residues, coupling of the protein to the surface can be brought about using conventional chemical cross-linking agents at a site remote from the main body of the protein. In this way, the covalent coupling process itself is less likely to interfere with the functionality of the protein.

EP 0434317 (Joseph Crosfield & Sons) discloses the use of improved affinity purification media which employ small specific binding agents, especially Fv antibody fragments. These optionally have a hydrophobic tail, with a particularly preferred linking group being the residue "Myc" amino acid sequence. Although such a group is primarily intended to facilitate immobilisation of the binding agent by non-covalent attachment onto a hydrophobic surface, it is mentioned in passing in the specification that as the myc group contains a lysine residue, it could also be used for covalent attachment onto surfaces.

Alternative peptide tails incorporating histidine residues have been used to attach proteins to nitrilotriacetic acid (NTA, manufactured by QIAGEN GmbH surfaces through the co-ordination of nickel. However, interactions of this type are non-covalent.

There remains a continuing need to improve the efficiency of the coupling reaction, however, and in particular to address the problems arising from the need to ensure that the protein is brought into association with the surface prior to the covalent coupling reaction. In case of coupling a protein to a negatively charged surface, such as a carboxymethyl activated dextran surface, for example, the coupling reaction must be performed at a low pH to ensure that the protein is positively charged in order for such association to occur. As many proteins are acid-sensitive, such conditions may have the effect of impairing the specific activity of the cross-linked protein. Not only would it be desirable to increase the amount of protein coupled to the surface but also to increase the proportion of coupled protein which retains its specific activity by minimising the possibility of non-specific binding interactions resulting from the protein unfolding under the coupling conditions.

SUMMARY OF THE INVENTION

In one aspect, the invention provides a material comprising a protein covalently coupled to a solid surface, wherein said protein comprises at least one polypeptide segment having one or more sites for covalent attachment, which polypeptide segment is capable of adopting a folded structure separate from the folded structure of the remainder of the protein. Also provided is the use of such a material in processes involving binding of molecules to the immobilised protein.

In another aspect, the invention provides a method for immobilising a protein at a solid surface comprising the steps of exposing a solid surface of a material to a solution of a protein comprising at least one polypeptide segment having one or more sites for covalent coupling, said segment being capable of adopting a folded structure separate from the folded structure of the remainder of the protein, and covalently coupling said protein to said surface.

Further provided is the use of a polypeptide segment capable of adopting a folded structure to facilitate covalent coupling of a protein to a solid surface.

The present invention may be more fully understood with reference to the following description, when read together with the accompanying drawings.

BRIEF DESCRIPTION OF THE DRAWINGS

FIG. 1 shows the nucleotide sequence of three pairs of complementary overlapping oligonucleotides used for the assembly of VHH antibodies with peptide tails (SW26 (SEQ ID NO: 3) and SW27 (SEQ ID NO: 5); SW28 (SEQ ID NO: 6) and SW29 (SEQ ID NO: 8); and SW30 (SEQ ID NO: 9) and SW31 (SEQ ID NO: 11)). Peptide sequence translation is marked below (SEQ ID NOS: 4, 7, and 10).

FIG. 4 shows diagrammatically the structure of the cassettes comprising the assembled VHH-tail encoding sequences which are inserted into the vector pPIC9 to give the constructs used for expression in *Pichia Pastoris*.

FIG. 5 shows a schematic representation of the proposed hairpin structure of the EKP tail.

FIG. 6 shows the pH-dependence of the amount of VHH-tail protein associating with a carboxymethylated surface as detected by surface plasmon resonance.

DETAILED DESCRIPTION OF THE INVENTION

Figure 2A:
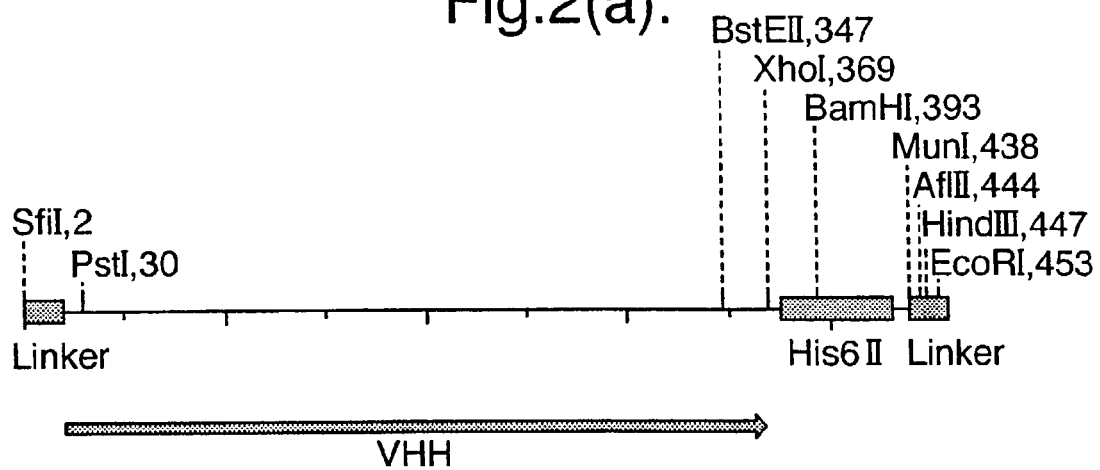
FIG. 2(a) shows a diagram showing a cassette comprising an anti-hCG VHH-encoding sequence which is inserted into pUC19 to give an intermediate vector (Vector A). This vector contains a Xho I site near the 3' end of the VHH-encoding DNA sequence, used for ligation of the annealed oligonucleotides encoding the tail sequences to the VHH and a Mun I site for ligation of the annealed oligonucleotides to the vector backbone.

The invention is based on the finding that the efficiency of covalent coupling of a protein to a solid surface may be enhanced by providing the protein with a polypeptide segment having one or more sites for covalent attachment which is capable of adopting a folded structure separate from the folded structure of the remainder of the protein.

By "folded" its meant a well defined three-dimensional structure which is held together by non-covalent forces.

Without wishing to be bound by theory, it is thought that by incorporating into the protein a polypeptide segment having one or more sites for covalent attachment in a locally ordered structure separate from the folded structure of the protein, the presentation of covalent coupling sites in the segment to suitable cross-linkable groups on the solid surface in an orientation appropriate for coupling to take place is facilitated. This leads to an increased likelihood of coupling of protein to surface occurring through the locally ordered polypeptide segment, which is not involved in protein binding and hence to increased coupling efficiency.

By improving the intrinsic association (or 'pre-concentration') of protein with the surface prior to coupling taking place, the invention advantageously affords the possibility of carrying out the covalent coupling reaction under conditions which are less likely to cause irreversible damage to protein functionality resulting from denaturation. In this way, non-specific binding interactions may be minimised as protein unfolding is reduced such that the proportion of coupled protein retaining its activity increases, decreasing the amount of material required to produce an active surface.

As shown in the Examples below, by means of the invention it is possible to raise the pH at which coupling of a protein to a negatively charged surface occurs, thereby reducing the likelihood of protein function being adversely affected by the coupling conditions used and so increasing coupling efficiency. This represents a significant advantage for the method of the invention over methods of coupling proteins to solid surfaces mediated by tails which are not capable of adopting a stable folded structure, such as the myc tail.

The invention is applicable to proteins in general and is not restricted to any particular grouping. Examples of suitable proteins include antibodies or immunologically active fragments thereof, receptors or binding fragments thereof, lectins and enzymes.

It will be appreciated that a solid surface may have more than one different protein immobilised on it in accordance with the present invention. These may be distributed evenly over the surface or immobilised in one or more discrete regions.

According to one important embodiment of the invention, antibodies or immunologically active fragments thereof may be immobilised at a solid surface to prepare improved immunoactive materials of use in immunological recognition procedures such as immunoaffinity techniques.

Suitably, the antibody is an immunoglobulin which may be derived from natural sources, or synthetically produced. The terms 'antibody' and 'immunoglobulin' are used synonymously throughout the specification unless otherwise indicated. An immunologically active antibody fragment is a portion of a whole antibody which retains the ability to exhibit antigen-binding activity. The antigen binding site may be formed through association of antibody light and heavy chain variable domains or may comprise individual antibody variable domains. Suitable fragments include an Fab fragment, containing both binding sites of an antibody connected together, an Fv fragment (comprising the variable domains of antibody heavy and light chains associated with each other) or a single chain Fv fragment (where both light and heavy chains are present as part of a fusion protein).

According to one particular embodiment of the invention, the protein is an immunoglobulin naturally devoid of light chains (hereinafter a heavy chain immunoglobulin), even more particularly a heavy chain variable domain of an immunoglobulin naturally devoid of light chains such as may be obtained from Camelids as described in WO 94/04678 (Casterman et al), or a protein functionally equivalent thereto. An advantage of using immunoglobulins or heavy chain variable domains from Camelids is that they can readily and conveniently be produced economically on a large scale, for example, using a transformed lower eukaryotic host as described in WO 94/25591.

With a heavy chain immunoglobulin, the antigen-binding capacity and specificity is located naturally and exclusively in the immunoglobulin heavy chains, more specifically in the heavy chain variable domains. That is, the heavy chain variable domain forms the complete antigen-binding site. By functionally equivalent is meant any protein or fragment or derivative thereof which has the same or similar antigen binding properties located in a single binding domain. It will be appreciated that immunoglobulins or fragments or derivatives thereof modified to enable them to function as binding domains in the same way as heavy chain immunoglobulins from Camelids (see Davies et al, Bio Technology, 13, 475-479, (1995)) may also suitably be used according to the invention.

The polypeptide segment according to the invention may be introduced by mutation or insertion within the protein sequence or preferably may be appended as a tail at either, or both of, the N- or C-terminus of the protein.

The polypeptide segment and the protein to which it is attached may conveniently be produced together by expression as a single fused protein in a genetically modified organism such that the protein and segment are linked through peptide bond(s). Alternatively, the protein and segment may be produced separately and attached by chemical conjugation, in which case the bond between the segment and protein will generally not be a peptide bond nor will the segment necessarily be attached at one end of the protein.

The polypeptide segment according to the invention conveniently comprises from 3 to 30 amino acid residues, preferably from 5 to 20 amino acid residues.

The polypeptide segment contains at least one, more preferably a plurality of cross-linkable residues for covalent attachment to a solid surface. It will be appreciated that the number of such cross-linkable residues is limited only by the requirement that the sequence remains capable of forming a folded structure. Conveniently, the polypeptide segment comprises from 2 to 15 cross-linkable residues for covalent attachment. Suitable reactive cross-linkable residues include cysteine and/or lysine residues. By providing the polypeptide segment with a plurality of such residues, the probability of coupling taking place via this segment is increased. This has the effect of enhancing coupling efficiency, and minimising coupling via residues elsewhere on the protein which could impair activity of the cross-linked protein.

Sequence features which may suitably be incorporated into the polypeptide segment in order to impart the propensity to form a folded structure according to the purposes of the invention would readily suggest themselves to those skilled in the art.

It will be appreciated it is not necessary for the operation of the invention that the whole of the polypeptide segment forms a folded structure, provided that at least part of it, most particularly a part comprising cross linkable residues can form a local folded structure. Conveniently, the polypeptide segment contains a spacer tail or tag in addition to that part which forms the folded structure such that the locally folded structure is held separate from the folded structure of the protein to which it is introduced.

Sequence features which promote the formation of α-helical or β-turn conformation are preferred. The presence of a folded structure may conveniently be detected using conventional techniques such as nuclear magnetic reasonable spectroscopy.

In one embodiment, the polypeptide segment for use according to the invention preferably comprises one or more proline residues.

Without wishing to be bound by theory, it is generally thought that the incorporation of a proline residue in the amino acid sequence of the polypeptide segment encourages the formation of a beta-turn structural configuration, with the peptide backbone changing direction about the proline residue.

According to another embodiment, the polypeptide segment comprises at least one, more preferably a plurality of pairs of oppositely charged amino acid residues capable of aligning against each other in a folded structure. Again, the number of pairs of oppositely charged amino acid residues is limited only by the requirement that the sequence remains capable of forming a folded structure. Typically, the sequence will comprise no more than 15 such pairs.

By incorporating oppositely charged amino acids in the sequence of the polypeptide segment in such a distribution that the formation of a folded structure would bring them into a favourable electrostatic configuration, the stability of the folded structure may be enhanced. Conveniently, the segment comprises two or more regions of alternating oppositely charged amino acid residues. Preferably, the regions of alternating oppositely charged amino acid residues are separated by a sequence which favours formation of a reverse turn compatible with pairing of opposite charges, especially by a sequence comprising one or more proline residue.

Preferred polypeptide segments for use according to the invention comprise an amino acid sequence of formula:

AZB wherein A and B are regions of peptide sequence that can come together to form a structure, and Z is a region of peptide sequence able to form a turn.

One embodiment of this generic structure is where A and B can be replaced by (XY)n and (XY)m, respectively giving the sequence:

$(XY)_n Z(XY)_m$ wherein X and Y are amino acids with opposite charge, n and m are the same or different and represent an integer from 2 to 15, and Z is a region of peptide sequence able to form a turn.

Particularly preferred polypeptide segments comprise an amino acid sequence selected from:—

EHHHHHHRSEKEKKPKEKEK (SEQ. ID. No. 1)

EHHHHHHRSGKGKKPKGKGK (SEQ. ID. No. 2)

hereinafter referred to as the EKP and GKP segments respectively.

It will be appreciated that the portion of the sequences comprising the amino acids EHHHHHHRS (SEQ ID NO: 12) corresponds to a poly His tag; its presence is not essential to the invention and this part of the sequence could be replaces with another conventional tag or deleted. For example, deletion of the poly His Tag (SEQ ID NO: 12) from the polypeptide sequences represented by SEQ ID NO: 1 and SEQ ID NO: 2 results in the peptide sequences EKEKKPKEKEK (SEQ ID NO: 13) and GKGKKPKGKGK (SEQ ID NO: 14), respectively.

As shown in FIG. 5, the segment having an amino acid sequence as set forth in SEQ. ID. No. 1 above (hereinafter referred to as the EKP segment) is thought to adopt a β-hairpin structural configuration, wherein the turn in the peptide backbone promoted by the presence of the proline residue in the sequence is stabilised by the electrostatic interaction of pairs of oppositely charged amino acid residues. This segment, especially when appended as a tail at one or both ends of the protein, represents a particularly preferred embodiment, of the invention.

As shown in the Examples below, by providing a protein with a polypeptide tail capable of adopting a folded structure not only is it possible to couple more protein to a solid surface but this coupling can be brought about under conditions which are less likely to result in protein denaturation and hence are less likely adversely to affect protein functionality, leading to an increased coupling efficiency.

Experiments to study coupling or proteins provided with either the EKP or GKP tails as described above or a control tail with no sequence features introducing structural characteristics (having the amino acid sequence EHHHHHHRS-GKGKKGKGKGK (SEQ ID NO: 4), hereinafter referred to as a GKG tail) to a carboxymethyl activated dextran surface have shown that demonstrably more protein couples to he solid surface when a structural tail is employed, the order of increase in amount reflecting increasing structural organization of the tail (GKG<GKP<EKP). Furthermore, by using the EKP tail to couple an anti-hCG VHH fragment to a carboxymethyl dextran surface, it has been demonstrated that it is possible to obtain an acceptable yield of immobilised protein, while increasing the proportion which retains its functionality, by carrying out the coupling reaction under less acidic conditions.

The solid surface to which the protein is immobilised according to the invention may be provided by a variety of materials. Suitably, the solid surface is any solid phase carrier material conventionally used in immobilising proteins. Examples include polystyrene or other plastics such as polypropylene or polyvinylchloride, celluloses, dextrans, synthetic polymers and co-polymers, latex, silicas, fabrics, metals such as gold, silver and platinum, carbon, glass. These materials may conveniently be particulate, such as polymeric beads or granules for columns, or in sheet form, for example membranes or filters, glass or plastic slides, microtitre assay plates, dipsticks, capillary fill devices or such like. The solid surface may alternatively comprise part of a mass-dependent biosensor such as an evanescent wave type sensor, for example a surface plasmon resonance detector such as may be obtained from Biacore AB, Stevenage, UK.

It will be appreciated that a solid surface for use according to the invention must be capable of being covalently coupled to the polypeptide segment. The solid surface may naturally comprise cross-linkable residues suitable for covalent attachment to the segment or it may be coated or derivatised to introduce suitable cross-linkable groups according to methods well known in the art.

Materials prepared according to the invention may be used in any process where it is useful to bind a molecule to an immobilised protein. Suitable applications will readily suggest themselves to the average skilled person in the art; these may include testing for the presence of a binding partner, for example, using a multiplicity of proteins bound to a solid surface according to the present invention in a protein array, or in assay or purification of a test sample. Where the protein is an antibody or an immunologically active fragment thereof, the immobilised materials may be used in immunoadsorption processes such as immunoassays, for example an enzyme-linked immuno-specific assay procedure (ELISA), or immunoaffinity purification processes by contacting a material according to the invention with a test sample according to standard methods conventional in the art.

It will be appreciated that the invention can be applied to proteins other than those derived from antibodies and the like. By way of example, enzymes can be coupled to surfaces for use in juice clarification. Other applications of immobilised proteins can be applied are described in In Protein Immobilisation, pp. 2-9, R. F. Taylor ed., Marcel Dekker, Inc., New York, 1991.

Conveniently, the invention may be employed in diagnostic test kits.

The following examples are provided by way of illustration only. Techniques used for the manipulation and analysis of nucleic acid materials were performed as described in Sambrook et al, Molecular Cloning, Cold Spring Harbor Press, New York, 2nd Ed., (1989), unless otherwise indicated.

VHH denotes heavy chain variable domain of a heavy chain immunoglobulin.

EXAMPLES

Construction of Tailed Antibody Fragments

Complimentary overlapping oligonucleotides (FIG. 1) were annealed and used to add peptide tail encoding DNA to an anti hCG VHH (clone number HI15) isolated from an immunised llama as described in WO 94/25591 according to the following steps:—

(I) VHH encoding DNA was isolated from the phage display vector (pHEN) via restriction digestion, using the enzymes Pst I/Bst EII, and was cloned into two pUC 19 intermediate vectors (A and B), modified to enable further manipulation via standard molecular biological techniques (FIGS. 2a and b).

Figure 3:
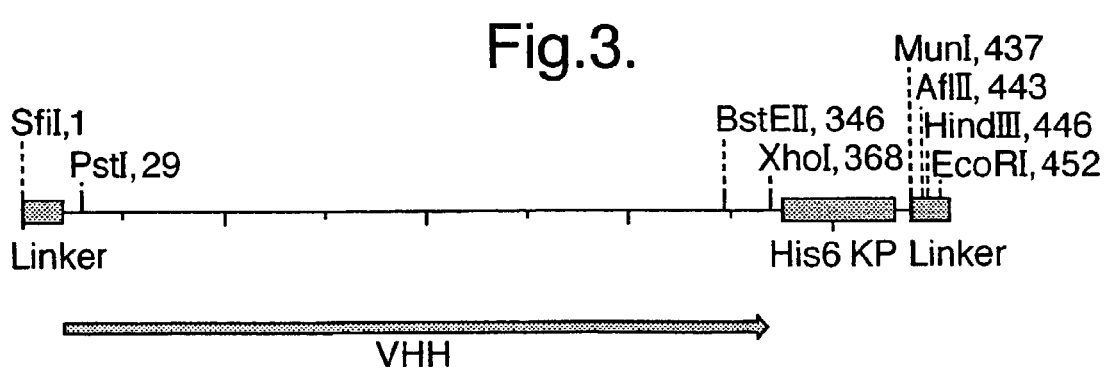
FIG. 3 shows diagrammatically the intermediate vector cassette obtained by ligation of the tail sequences to the 3' end of the VHH-encoding sequence in Vector A.

(II) 2 µg of each overlapping oligonucleotide pair (FIG. 1) were mixed in a 50 µl volume, heated for 5 minutes at 98° C. then cooled on ice to anneal. Oligonucleotide primer pairs were:—SW26 and SW27 (used for the assembly of the GKG tail sequence, a control sequence with no structural organisation), SW28 and SW29 (GKP tail sequence) and SW30 and SW31 (EKP tail sequence). Intermediate vector (A) was isolated and digested with enzymes Xho I and Mun I. Vector and annealed primer pairs were ligated, introducing the peptide tail encoding DNA (FIG. 3).

Figure 2B:
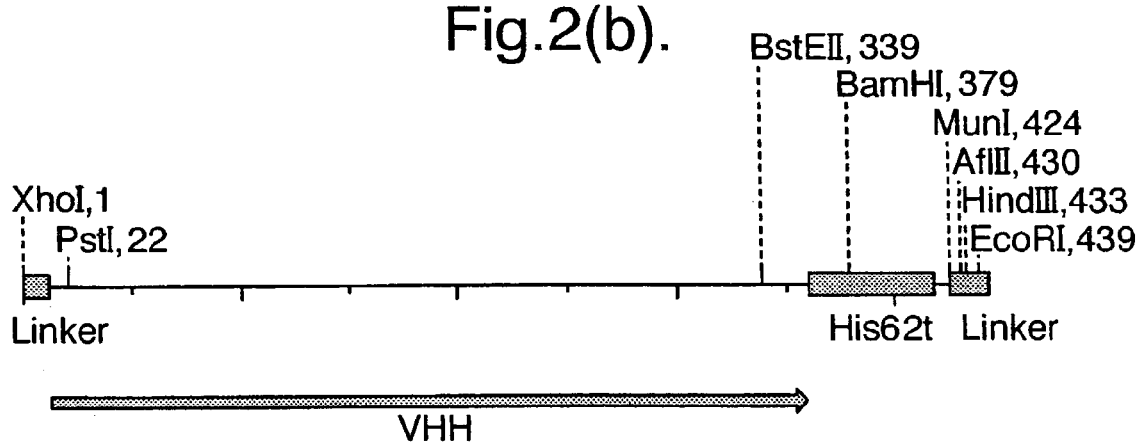
FIG. 2(b) shows a diagram showing a cassette comprising the VHH encoding sequence which is inserted into pUC19 to give the intermediate construct (Vector B). This intermediate vector cassette contains a XhoI site at the 5' end of the VHH-encoding DNA sequence, which is in the correct reading frame for cloning into the *Pichia Pastoris* expression vector pIC9.

(III) The VHH-tail DNA fusions were introduced into the *Pichia pastoris* expression vector pPIC 9 as three point ligations (one for each tail format). Vector A clones, containing correctly inserted VHH DNA were digested with Bst EII and Eco RI (tail DNA inserts were collected). Vector B, (FIG. 2b) was digested Xho I/Bst EII (VHH insert was collected). pPIC 9 Vector DNA was digested Xho I/Eco RI (vector backbone collected). Insert, vector and tails were ligated and transformed into the *E. coli* strain XL1-B using standard molecular biological techniques, creating the final constructs.

(IV) DNA comprising the final constructs was isolated from overnight cultures inoculated with single colonies taken from plated transformations, using a Qiagen plasmid midiprep kit as per the manufacturers' instructions. The constructs were verified as correctly assembled by automated DNA sequence analysis. 5 µg of each construct was digested with the restriction enzyme Bgl II, followed by phenol extraction, chloroform extraction and ethanol precipitation. Pelleted DNA was washed twice with 70% ethanol (to remove salts) air dried and resuspended in 5 µl dH$_2$O. Bgl II digested pPIC 9 vector, containing the modified VHH DNA, was transformed into *Pichia pastoris* strain GS115 according to the method of step (V).

(V) Cells were grown overnight at 30° C., in 500 ml YPD medium (1% yeast extract, 2% peptone, 1% glucose) to an OD$_{600}$ of 1.4. The cells were spun (3 min. 2.5 Kg) and the pellet was washed with sterile distilled water before resuspending in 100 ml KDTT buffer (50 mM KH$_2$PO$_4$ pH 7.5 plus 25 mM dithiothreotol). After 15 min. incubation at 37° C. the cells were pelleted as before and resuspended in 100 ml ice cold STM buffer (10 mM Tris. Cl pH 7.5 plus 1 mM MgCl$_2$ and 92.4 g glucose per liter). After 5 washes with this buffer the cell pellet was resuspended into a final volume of 3 ml STM buffer. Digested DNA (in a volume of 5 µl) was mixed with 70 µl competent cells on ice. The cells were electroporated in a 0.2 cm cuvette at 1.5 kV, 400Ω, 25 µF in a BioRad Gene-Pulser. Immediately after electroporation, 1 ml YPD medium was added to the cells. After recovery for 1 hour at 37° C. the cells were plated out onto 3×MD plates. Colonies formed by transformed cells (His+) were visible within 48 hours incubation at 30° C.

Expression and Purification of Antibody Fragments

Anti hCG VHHs containing peptide tails were expressed in *Pichia pastoris* according to the following method.

Colonies from freshly transformed *P. pastoris* were replica plated onto MD and MM plates as described in the Invitrogen *Pichia* expression kit (version B) users manual. The plates were incubated for 48 hours at 30° C., at which point mut-s clones were selected (visualised by the presence of much smaller colony growth on MM plates). 6-12 colonies of each VHH type were "stabbed" from the MD plates (corresponding to the mut-s colonies identified from the MM plates) and used to inoculate 10 ml of BMGY media. The 10 ml cultures were incubated at 30° C. for 20 hours and were then pelleted by centrifugation. 2 ml BMMY was used to replace the media for each culture, which were then incubated for a further 20 hours. 10 µl methanol (100%) was added and the cultures were incubated for a final 24 hours before being pelleted again.

Expression supernatants were evaluated for VHH production using an NTA sensor chip (to bind the His6 tags that made up part of each VHH tail type) in a Biacore 2000 instrument. Each supernatant was diluted 1/50 in HBS buffer containing 50 µM EDTA. 15 µl diluted sample was passed over the surface (after first priming the surface with 15 µl of 0.5 mM $Ni_2SO_4$). After sample addition the sensor surfaces were regenerated using 15 µl 0.35M EDTA. Flow rate was set to 15 µl/min throughout. Isolated colonies that generated expression supernatants with the highest production levels were re-cultured overnight in BMGY, and were stored until required in 15% glycerol at –70° C.

Large scale shake flask expression was conducted as described in the Invitrogen *Pichia* Users Manual, using 2 L baffled shake flasks, with a liquid volume of 0.5 L. Forty-eight hours after induction, the cultures were harvested by centrifugation at 18,112 g (1 hour at 4° C.) and then the supernatants were filtered through 0.45 µm Nalgene filter units.

Purification of the VHHs was via the use of commercially available Ni-NTA Superflow resin (Qiagen corp.), which has a capacity of 5-10 mg of 6×His-tagged protein per ml of resin. Before starting, the pH of the load (expression supernatant) was adjusted to 6 or greater in order to ensure high affinity interaction between the His6 tagged VHHs and the resin.

10-20 ml of resin was packed into chromatography columns, which were washed with 5 bed volumes of wash buffer (e.g. PBSA or 10 mM potassium phosphate buffer pH 6). This and all subsequent steps were performed at a flow rate of 2 mL/min.

Supernatants were loaded onto the column and then washed with about 10 column volumes of wash buffer, 5 column volumes of 1 M NaCl, then again with wash buffer until the optical density at 280 nm reached the baseline. Elution of VHH was via a linear gradient of 0-0.5 M imidazole over 10 column volumes followed by desalting through a 200 ml sephadex G25 desalting column. The purity of VHHs isolated using this methodology was estimated to be 99% or greater.

Interaction of Tailed Antibody Fragments with Carboxymethyl Dextran

A CM5 Sensor chip (Biacore AB, Sweden) was docked in a Biacore 2000 biosensor (Biacore AB, Sweden) and an experiment was performed as follows:—

The flow rate was set to 10 ul/min and 20 ul of VHH115EKP (made up in 10 mM sodium citrate pH 4.0) was injected across the sensor surface. This was repeated using VHH115EKP made up in sodium citrate buffer at pH 4.0, 4.2, 4.4, 4.6, 4.8, 5.1, 5.4, 5.8 and 6.0. The amount of protein interacting with the sensor surface during the injection was determined.

A further experiment was then performed in which injections of VHH115GKP (20 ul made up in 10 mM Tris pH 5.8, 6.0, 6.2, 6.4, 6.6, 6.8, 7.0, 7.2, 7.4 and 7.6) and injections of VHH115GKG (20 ul made up in 10 mM Tris pH 5.8, 6.0, 6.2, 6.4, 6.6, 6.8, 7.0, 7.2, 7.4 and 7.6) were made across a CM5 biosensor surface.

The amount of antibody fragment associating with the chip surface was plotted at the different pH's and can be seen in FIG. 6. The data shown with the solid lines are those samples made up in sodium citrate buffer, whereas the data shown with the dashed lines are those samples made up in Tris buffer.

The antibody fragment VHH115EKP associated with the CM5 sensor surface to a greater extent at higher pH than either of the other two fragments. This is due to the decreased pI of this protein brought about by the introduction of glutamic acid residues in the peptide tail.

Coupling Tailed Antibody Fragments to Carboxymethyl Dextran

Antibody fragments VHH115EKP, VHH115GKP and VHH115GKG were covalently coupled to a CM5 sensor surface as follows:

A new CM5 sensor chip was docked in the Biacore and a sensorgram was obtained as follows. The flow path set to 1-2-3-4 and the flow rate of HBS set to 10 µl/min. The flow path was changed to flow only through flow cell 1 and VHH115EKP was coupled using an amine coupling kit as described by the manufacturers. Briefly, 40 µl of a mixture of N-hydroxysuccinimide ester (NHS) and ethylenediamine carboimide (EDC) was quickinjected across flow cell 1 to activate the sensor surface. This was followed by a 20 µl quickinjection of VHH115EKP diluted 1 in 50 in 10 mM sodium citrate buffer pH 5.4. The sensor surface was blocked by a quickinjection of 40 µl ethanolamine (1M) across flow cell 1. The flow path was then changed to flow only across flow cell 2 and VHH115GKP was amine coupled. Briefly, 40 µl of a mixture of NHS/EDC was quickinjected across flow cell 2 to activate the sensor surface. This was followed by a 20 µl quickinjection of VHH115GKP diluted 1 in 50 in 10 mM sodium citrate buffer pH 4.0. The sensor surface was blocked by a quickinjection of 40 µl ethanolamine (1M) across flow cell 2. The flow path was then changed to flow only across flow cell 3 and VHH115GKG was amine coupled. Briefly, 40 µl of a mixture of NHS/EDC was quickinjected across flow cell 3 to activate the sensor surface. This was followed by a 20 µl quickinjection of VHH115GKG diluted 1 in 50 in 10 mM sodium citrate buffer pH 4.7. The sensor surface was blocked by a quickinjection of 40 µl ethanolamine (1M) across flow cell 3.

The particular coupling pH for each fragment was chosen as at these pH's the fragments all associated with the CM5 surface to the same extent (see FIG. 6). The amount of fragment coupled to the various flow cells is shown in Table 1 below. It can be seen from the results presented in Table 1 that more protein is coupled when a structured tail is used.

TABLE 1

| Fragment | Amount coupled (Response Units) |
|---|---|
| VHH115EKP | 513.2 |
| VHH115GKP | 258.3 |
| VHH115GKG | 223.5 |

In this experiment, the individual coupling pHs chosen were such that the extent of non-covalent association in advance of the coupling reaction was the same for all three proteins. The finding that the amount of protein coupled is not the same in all three cases therefore indicates that efficiency of cross-linking does not depend solely on the amount of protein non-covalently associated with the surface. The results obtained demonstrate the influence of the tail structure and pH on coupling efficiency, the amount of protein coupled increasing in an order reflecting the increase in structural organisation of the tail (GKG<GKP<EKP).

Coupling VHH115EKP Tailed Fragment to Carboxymethyl Dextran at Various pH's

A new CM5 sensor chip (chip 2) was docked in the Biacore and a sensorgram was run. The flow path set to 1-2-3-4 and the flow rate of HBS set to 10 µl/min. The flow path was changed to flow only through flow cell 1 and VHH115EKP was coupled using an amine coupling kit as described by the manufacturers. Briefly, 40 µl of a mixture of NHS/EDC was quickinjected across flow cell 1 to activate the sensor surface. This was followed by a 20 µl quickinjection of VHH115EKP diluted 1 in 50 in 10 mM sodium citrate buffer pH 4.0. The sensor surface was blocked by a quickinjection of 40 µl ethanolamine (1M) across flow cell 1. The flow path was then changed to flow only across flow cell 2 and VHH115EKP was amine coupled by quickinjecting 40 µl of a mixture of NHS/EDC across flow cell 2 to activate the sensor surface. This was followed by a 20 µl quickinjection of VHH115EKP diluted 1 in 50 in 10 mM sodium citrate buffer pH 4.6. The sensor surface was blocked by a quickinjection of 40 µl ethanolamine (1M) across flow cell 2. The flow path was then changed to flow only across flow cell 3 and VHH115EKP was amine coupled. Briefly, 40 µl of a mixture of NHS/EDC was quickinjected across flow cell 3 to activate the sensor surface. This was followed by a 20 µl quickinjection of VHH115EKP diluted 1 in 50 in 10 mM sodium citrate buffer pH 5.1. The sensor surface was blocked by a quickinjection of 40 µl ethanolamine (1M) across flow cell 3.

The amounts of VHH115EKP coupled under the different pH's is shown in Table 2.

TABLE 2

| VHH115EKP coupling pH | Amount coupled (Response Units) |
|---|---|

Capture of Human Chorionic Gonadotrophin (hCG) to Coupled VHH115EKP 554.0

The sensor chip (chip 2) was docked in the Biacore 2000 and a sensorgram was run. The flow path was set to flow through 1-2-3-4 and the flow rate set to 10 µl/min. A 40 µl sample of hCG (50 IU/ml) was injected across flow cells 1-4. The sensorgram traces resulting from the injection were overlayed in the software package BIAevaluation (Biacore AB) and the background from flow cell 4 was subtracted from all flow channels.

Overlayed traces of hCG binding to VHH115EKP coupled surfaces are shown in FIG. 9 (fine line, flow cell 3; medium line, flow cell 2; thick line, flow cell 1). The amount of hCG bound when the binding curve reached a plateau is shown in Table 3. The maximum amount of hCG expected to bind to the coupled VHH115EKP fragment can be determined by the following equation:

$$\text{Maximum binding} = A * M1/M2$$

Where, A is the amount of VHH115EKP coupled, M1 is the molecular weight of hCG (38000 Da) and M2 is the molecular weight of VHH115EKP (15000 Da).

The amount of hCG binding can be expressed as a percentage of the maximum binding, this data is shown in Table 3.

TABLE 3

| VHH115EKP coupling pH | hCG bound | Maximum binding | PMB |
|---|---|---|---|
| 4.0 | 567 | 1403 | 40 |
| 4.6 | 518 | 1076 | 48 |
| 5.1 | 237 | 253 | 94 |

PMB, percentage of maximum binding, where the molecular weight of hCG and VHH115EKP is 38000 and 15000 Da, respectively.

It can be seen as the pH is decreased, although the amount of captured hCG increases, it does not increase in proportion to the total amount of protein cross-linked, indicating that a greater proportion of the cross-linked protein loses function when the coupling pH is lower. This demonstrates the potential importance of being able to achieve a good coupling efficiency at a higher (more moderate) coupling pH by using the method according to the present invention.

The invention claimed is:

1. A material comprising a protein covalently coupled to a solid surface via at least one polypeptide having one or more sites for covalent attachment, wherein the polypeptide comprises a sequence as set forth in SEQ ID NO: 1, 2, 13 or 14.

2. The material of claim 1, wherein the polypeptide consists of the sequence as set forth in SEQ ID NO: 1, 2, 13 or 14.

3. The material according to claim 1, wherein the solid surface is selected from the group consisting of polystyrene, polypropylene, polyvinylchloride, celluloses, dextrans, synthetic polymers and co-polymers, latex, silica, fabric, metal, carbon, and glass.

4. The material according to claim 1, constituting all or part of a microtitre plate, a dipstick, a slide, a column or polymeric beads.

5. A method of binding a molecule to an immobilised protein comprising providing the material of any one of claims 2, 3, or 4 and exposing the material to a molecule, whereby the molecule binds to the immobilised protein on the material.

6. The method of claim 5, wherein the protein comprises an antibody or a fragment thereof.

7. The method of claim 6, wherein the method comprises an immunoassay.

8. A method for affinity purification of a molecule comprising contacting the material according to any one of claims 1, 3, or 4 with a sample comprising the molecule and isolating the purified molecule from the sample.

9. A method for immobilising a protein at a solid surface comprising exposing a solid surface of a material to a solution of a protein comprising at least one polypeptide comprising the amino acid sequence as set forth in SEQ ID NO: 1, 2, 13 or 14 and covalently coupling the protein to the surface.

10. The method of claim 9, wherein the method comprises a protein assay comprising immobilising a plurality of individual proteins on a solid surface according to the method of claim 9.

11. A polypeptide comprising the amino acid sequence as set forth in SEQ ID NO: 1, 2, 13 or 14.

12. The polypeptide of claim 11, wherein the polypeptide consists of the amino acid sequence as set forth in SEQ ID NO 1, 2, 13 or 14.

13. A method of facilitating covalent coupling of a protein to a solid surface comprising exposing a solid surface of a material to a solution of a protein comprising at least one polypeptide according to claim 11 and covalently coupling the protein to the surface.

* * * * *

SEQUENCE LISTING

<160> NUMBER OF SEQ ID NOS: 14

<210> SEQ ID NO 1
<211> LENGTH: 20

-continued

```
<212> TYPE: PRT
<213> ORGANISM: Artificial Sequence
<220> FEATURE:
<223> OTHER INFORMATION: Description of Artificial Sequence: LINKER
      SEQUENCE

<400> SEQUENCE: 1

Glu His His His His His His Arg Ser Glu Lys Glu Lys Lys Pro Lys
 1               5                  10                  15

Glu Lys Glu Lys
            20

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: LINKER
      SEQUENCE

<400> SEQUENCE: 2

Glu His His His His His His Arg Ser Gly Lys Gly Lys Lys Pro Lys
 1               5                  10                  15

Gly Lys Gly Lys
            20

<210> SEQ ID NO 3
<211> LENGTH: 69
<212> TYPE: DNA
<213> ORGANISM: Artificial Sequence
<220> FEATURE:
<223> OTHER INFORMATION: Description of Artificial Sequence: SYNTHETIC
      PLASMID INSERT ENCODING PEPTIDE TAIL
<220> FEATURE:
<221> NAME/KEY: CDS
<222> LOCATION: (3)..(62)

<400> SEQUENCE: 3 tc gag cac cat cac cat cac cat cgt tct ggt aag ggt aag aag gga      47
   Glu His His His His His His Arg Ser Gly Lys Gly Lys Lys Gly
    1               5                  10                  15 aag ggt aag ggt aag taataac                                         69
Lys Gly Lys Gly Lys
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: SYNTHETIC
      PLASMID INSERT ENCODING PEPTIDE TAIL

<400> SEQUENCE: 4

Glu His His His His His His Arg Ser Gly Lys Gly Lys Lys Gly Lys
 1               5                  10                  15

Gly Lys Gly Lys
            20

<210> SEQ ID NO 5
<211> LENGTH: 69
<212> TYPE: DNA
<213> ORGANISM: Artificial Sequence
<220> FEATURE:
<223> OTHER INFORMATION: Description of Artificial Sequence: SYNTHETIC
      PLASMID INSERT ENCODING PEPTIDE TAIL
```

```
<400> SEQUENCE: 5
aattgttatt acttaccctt accctttccc ttcttaccct taccagaacg atggtgatgg      60
tgatggtgc                                                              69

<210> SEQ ID NO 6
<211> LENGTH: 69
<212> TYPE: DNA
<213> ORGANISM: Artificial Sequence
<220> FEATURE:
<223> OTHER INFORMATION: Description of Artificial Sequence: SYNTHETIC
      PLASMID INSERT ENCODING PEPTIDE TAIL
<220> FEATURE:
<221> NAME/KEY: CDS
<222> LOCATION: (3)..(62)

<400> SEQUENCE: 6 tc gag cac cat cac cat cac cat cgt tct ggt aag ggt aag aag cca        47
   Glu His His His His His His Arg Ser Gly Lys Gly Lys Lys Pro
   1               5                  10                  15 aag ggt aag ggt aag taataac                                            69
Lys Gly Lys Gly Lys
            20

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: SYNTHETIC
      PLASMID INSERT ENCODING PEPTIDE TAIL

<400> SEQUENCE: 7

Glu His His His His His His Arg Ser Gly Lys Gly Lys Lys Pro Lys
1               5                  10                  15

Gly Lys Gly Lys
            20

<210> SEQ ID NO 8
<211> LENGTH: 69
<212> TYPE: DNA
<213> ORGANISM: Artificial Sequence
<220> FEATURE:
<223> OTHER INFORMATION: Description of Artificial Sequence: SYNTHETIC
      PLASMID INSERT ENCODING PEPTIDE TAIL

<400> SEQUENCE: 8
aattgttatt acttaccctt accctttggc ttcttaccct taccagaacg atggtgatgg      60
tgatggtgc                                                              69

<210> SEQ ID NO 9
<211> LENGTH: 69
<212> TYPE: DNA
<213> ORGANISM: Artificial Sequence
<220> FEATURE:
<223> OTHER INFORMATION: Description of Artificial Sequence: SYNTHETIC
      PLASMID INSERT ENCODING PEPTIDE TAIL
<220> FEATURE:
<221> NAME/KEY: CDS
<222> LOCATION: (3)..(62)

<400> SEQUENCE: 9 tc gag cac cat cac cat cac cat cgt tct gag aag gag aag aag cca        47
   Glu His His His His His His Arg Ser Glu Lys Glu Lys Lys Pro
   1               5                  10                  15 aag gag aag gag aag taataac                                            69
```

-continued

Lys Glu Lys Glu Lys
            20

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: SYNTHETIC
      PLASMID INSERT ENCODING PEPTIDE TAIL

<400> SEQUENCE: 10

Glu His His His His His His Arg Ser Glu Lys Glu Lys Pro Lys
 1               5                  10                  15

Glu Lys Glu Lys
            20

<210> SEQ ID NO 11
<211> LENGTH: 69
<212> TYPE: DNA
<213> ORGANISM: Artificial Sequence
<220> FEATURE:
<223> OTHER INFORMATION: Description of Artificial Sequence: SYNTHETIC
      PLASMID INSERT ENCODING PEPTIDE TAIL

<400> SEQUENCE: 11
aattgttatt acttctcctt ctcctttggc ttcttctcct tctcagaacg atggtgatgg      60
tgatggtgc                                                             69

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: SYNTHETIC
      PLASMID INSERT ENCODING PEPTIDE TAIL

<400> SEQUENCE: 12

Glu His His His His His His Arg Ser
 1               5

<210> SEQ ID NO 13
<211> LENGTH: 11
<212> TYPE: PRT
<213> ORGANISM: Artificial sequence
<220> FEATURE:
<223> OTHER INFORMATION: Polypeptide segment

<400> SEQUENCE: 13

Glu Lys Glu Lys Lys Pro Lys Glu Lys Glu Lys
 1               5                  10

<210> SEQ ID NO 14
<211> LENGTH: 11
<212> TYPE: PRT
<213> ORGANISM: Artificial sequence
<220> FEATURE:
<223> OTHER INFORMATION: Polypeptide segment

<400> SEQUENCE: 14

Gly Lys Gly Lys Lys Pro Lys Gly Lys Gly Lys
 1               5                  10